United States Patent [19]

Lichtenberg

[11] 4,320,340
[45] Mar. 16, 1982

[54] APPARATUS FOR MEASURING MAGNETIC FLUX DENSITY RESULTING FROM GALVANIC CURRENT FLOW IN SUBSURFACE CASING USING A PLURALITY OF FLUX GATES

[75] Inventor: Heinz D. Lichtenberg, Houston, Tex.
[73] Assignee: Dresser Industries, Inc., Dallas, Tex.
[21] Appl. No.: 74,834
[22] Filed: Sep. 13, 1979
[51] Int. Cl.³ .................... G01N 27/72; G01R 33/04
[52] U.S. Cl. .................................... 324/221; 324/253
[58] Field of Search ........ 324/220, 221, 244, 253–255, 324/219, 242, 243, 54, 52, 71 R, 346

[56] References Cited

U.S. PATENT DOCUMENTS

| | | | |
|---|---|---|---|
| 2,553,350 | 5/1951 | Bayhi | 324/221 |
| 2,770,773 | 11/1956 | Cooley | 324/221 |
| 2,870,541 | 1/1959 | Mayes | 324/220 X |
| 2,940,302 | 6/1960 | Scherbatskoy | 324/220 X |
| 2,992,390 | 7/1961 | DeWitte | 324/220 |
| 3,056,920 | 10/1962 | Herrald | 324/221 |
| 3,064,127 | 11/1962 | Green et al. | 324/220 X |
| 3,189,819 | 6/1965 | Schmidt | 324/220 X |
| 3,202,914 | 8/1965 | Deem et al. | 324/242 |
| 3,218,547 | 11/1965 | Ling | |
| 3,243,697 | 3/1966 | Schmidt | 324/221 |
| 3,246,219 | 4/1966 | Devol et al. | |
| 3,284,702 | 11/1966 | Ownby | 324/220 |
| 3,453,531 | 7/1969 | Warren | |
| 3,745,452 | 7/1973 | Osburn et al. | 324/254 X |
| 3,899,734 | 8/1975 | Beaver et al. | 324/220 |
| 4,061,965 | 12/1977 | Nelson | 324/52 X |

FOREIGN PATENT DOCUMENTS 700751 12/1953 United Kingdom.
1248567 10/1971 United Kingdom.

OTHER PUBLICATIONS

Scott, Gordon N., "*An Outline of Some Problems In Oil Well Casing Corrosion,*" Paper presented at Spring Meeting of Pac. Coast Dist. of Prod. of API, May. 13–14, 1949.

*Primary Examiner*—Gerard R. Strecker
*Attorney, Agent, or Firm*—Richard M. Byron; Patrick H. McCollum

[57] ABSTRACT

An improved well logging method and apparatus is provided for more reliable and accurate detection of corrosion in subsurface well casing. Method and apparatus are described for measuring the density of the flux field established inside the casing due to galvanic current flow longitudinally within the casing. A subsurface instrument housing a plurality of flux gates traverses the interior of the casing measuring the flux density within the casing. As the instrument comes proximate a corrosion location there will be detected a change in flux density due to current flowing from the casing into the formation. The detected change is transmitted to a surface location to provide an indication of the location and depth of corrosion.

3 Claims, 8 Drawing Figures

FIG. 4a
4b
4c
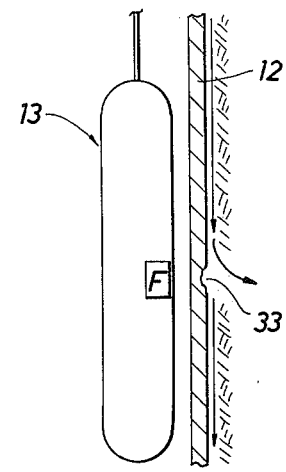
FIG. 5
FIG. 6
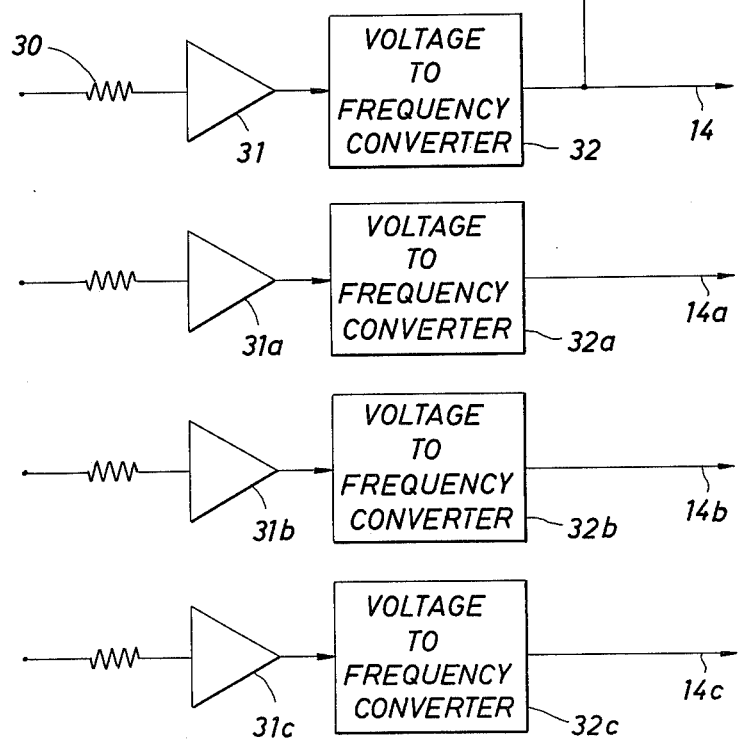

APPARATUS FOR MEASURING MAGNETIC FLUX DENSITY RESULTING FROM GALVANIC CURRENT FLOW IN SUBSURFACE CASING USING A PLURALITY OF FLUX GATES

BACKGROUND OF THE INVENTION

This invention relates to improved methods and apparatus for, the detection of corrosion in subsurface oil well casing, and more particularly relates to methods and apparatus for the detection of casing corrosion by the measurement of the current density profile within the casing.

It is well known in the oil and gas industry to set steel subsurface pipe, casing, in wells prior to the well being placed into production. Electrochemical theory postulates a tendency for steel, or other metals, in an electrolytic environment, such as subsurface formations to go into solution. Such tendency will tend to vary with the composition of the environment. Hence, it would be expected that differences in potential would exist on a long continuous electrical conductor, like oil well casing, in contact with various geological formations and it would also be expected that current would flow in the casing as a consequence of these differences in potential. Current flow of this type is referred to as galvanic current.

The passage of current in either direction between the casing and the formation is accompanied by chemical changes related in a complex way to the strength of the current and its time of passage. If the casing gaines current, hydrogen gas is deposited on the metal. If the casing loses current, iron is carried into solution. In either event, the immediate environment of the casing changes. It has been shown that a discharge of one ampere of current from the casing for a one year period carries with it twenty pounds of iron.

One method of reversing the corrosion on casing caused by galvanic current flow consist of balancing the corrosive current with an equal and opposite current in order to cancel the corrosive current. This process is termed cathodic protection. In this process a direct current from an external source is used to make the entire casing string a cathode.

Prior art methods of detecting casing corrosion and monitoring the success of cathodic protection have consisted of measuring the voltage drop along an interval of casing. A typical instrument to measure the voltage drop consists of upper and lower spaced contactors. These contactors are in the form of knife-shaped edges or spiked rotating wheels and are separated by an interval which can be up to fifty feet. The contactors are biased into integral contact with the inside of the casing and record measurement of the voltage differential between the two contact points. Successive interval measurements provide a depth related log of the length of the well casing.

Such method and apparatus as the above described suffer from several short comings. The instrument requires a metal to metal contact between the tool and casing. Mill scale, rust, and wax deposits interfere with good contact and can result in a meaningless measurement. Further, to make a differential voltage measurement over a span of casing the resistance per foot of the casing must be known. Casings from different manufacturers and of different weights and sizes have different resistances making the resistance per foot a difficult turn to establish.

These and other disadvantages are overcome with the present invention by providing method and apparatus for measuring the current density profile within the casing by detecting the flux density within the borehole caused by galvanic current flow within the casing.

SUMMARY OF THE INVENTION

In a preferred embodiment of the invention, a well logging system is provided which, in its overall concept includes an elongated housing for traversing a borehole. The elongated housing will contain a plurality of flux gates, located about the same plane of elevation within the housing, and orientated in a like manner for measuring the density of the flux field at a level within the casing. The measured signals are coupled to a subsurface electronics assembly for processing. Within the subsurface electronics a sample/hold circuit converts the measured signal from the respective flux gate to a functionally related d.c. potential. The d.c. level signal is filtered by means of a low pass filter and coupled along with the d.c. levels representative of the other measured flux density signals into the input of a summing amplifier. The summed output of the amplifier is coupled to a voltage to frequency converter the output of which will be an alternating frequency signal functionally related to the level of the summed d.c. input and thus proportional to the density of the flux field within the casing. The measured flux field density is functionally related to current flow within and from the well casing thus indicating casing corrosion.

The output from the voltage to frequency converter is transmitted over a logging cable to a surface electronics. Circuitry within the surface electronics reconverts the received alternating frequency signal to a d.c. level signal which is then recorded. The recorded signal is representative of the measured flux density within the casing, the magnitude of which will be substantially altered by a change in current flow within the casing as caused by casing corrosion.

Accordingly, it is a feature of the present invention to provide method and apparatus for the measurement of galvanic current flow within well casing by detecting the flux density within the borehole.

It is yet another feature of the present invention to provide method and apparatus for the detection of well casing corrosion by the measurement of the flux field density within the borehole.

It is another feature of the present invention to provide method and apparatus for determining the presence and orientation of corrosion locations on subsurface well casing. A particular feature of the present invention is to provide method and apparatus for detecting the density of the flux field about a level within the casing, converting the detected flux density signal into a d.c. level signal functionally related to the detected flux field, producing an alternating frequency signal representative of the level of the d.c. potential, transmitting the frequency representation to a surface location for conversion to a recordable signal the magnitude of which indicates the location of corrosion on the casing.

Another particular feature includes circuitry for generating a representation of the orientation of detected corrosion on the casing.

These and other features and advantage of the present invention can be understood from the following description of several techniques of producing the invention described in conjunction with the following drawings.

BRIEF DESCRIPTION OF THE DRAWING

FIGS. 4a, 4b, and 4c graphically illustrate signals present at various locations within the circuitry of FIG. 3.

FIG. 5 is a simplified representation of the operational theory of the subsurface instrument.

FIG. 6 is a simplified functional representation of orientation circuitry combined with a portion of the subsurface circuitry.

DETAILED DESCRIPTION OF THE DRAWINGS

Figure 1:
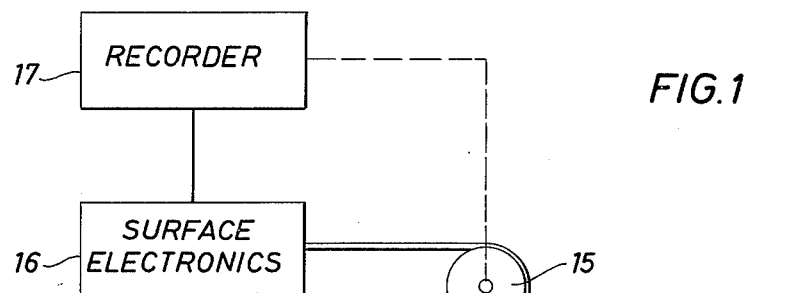
FIG. 1 is a simplified functional overall representation of an embodiment of the present invention.

Referring now to the drawings in more detail, FIG. 1 illustrates a portion of the earth's surface 10 into which a borehole 11 has been drilled. A casing string 12 has been placed within the borehole and cemented in place. Disposed within the borehole and adapted to be raised and lowered therein is borehole instrument 13 supported by cable 14 from the earth's surface. The apparatus on the surface of the earth consists of measuring wheel 15 over which cable 14 passes and a drum (not shown) on which cable 14 is wound, or from which it is unwound, when instrument 13 is caused to traverse borehole 11. Cable 14 contains the necessary conductor for transmitting information from instrument 13 to surface electronics 16 and carrying power for operation from surface electronics 16 to instrument 13. Surface electronics 16 is coupled to recorder 17 which makes a permanent record of the well logging data. Such a recorder might be a penchart recorder, an oscilloscope or other recording device well known in the industry. Measuring wheel 15 is also connected to recorder 17 which causes the recorder to record the subsurface measurement as a function of depth within the borehole in the conventional manner. Located within instrument 13 is subsurface electronics 18 and flux gate assembly 19, the operation of which will be explained with reference to subsequent drawings.

Figure 2:
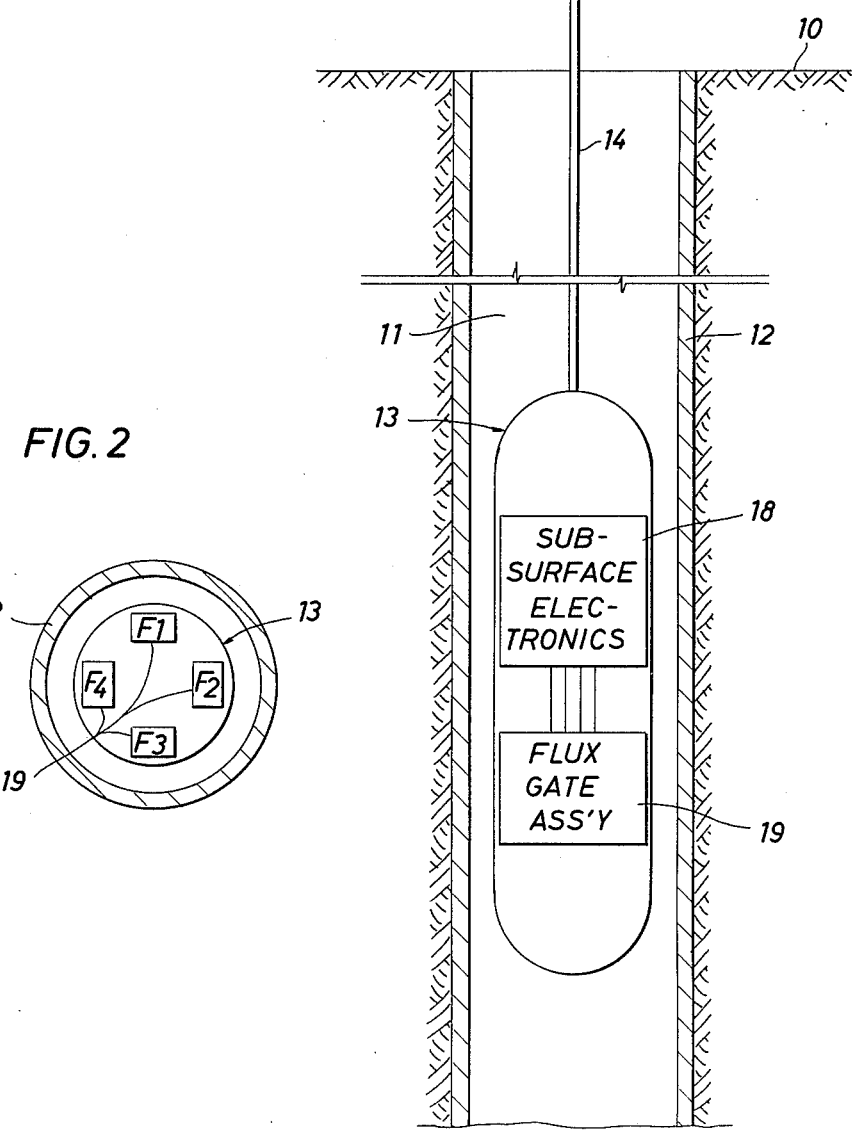
FIG. 2 is a more detailed functional representation of the subsurface flux gate assembly of the subsurface instrument.

Referring now to FIG. 2, there is illustrated the flux gate assembly 19 of instrument 13 within casing 12. In the preferred embodiment, flux gate assembly 19 is comprised of four flux gates, $F_1$–$F_4$, of the type described in my copending U.S. patent application No. 960,679 now U.S. Pat. No. 4,205,266. The flux gates are aligned within instrument 13 so that each flux gates' axis of sensitivity is perpendicular to the longitudinal current flow within casing 12. The alignment allows all four flux gates to measure the same flux field in a reinforcing manner.

Figure 3:
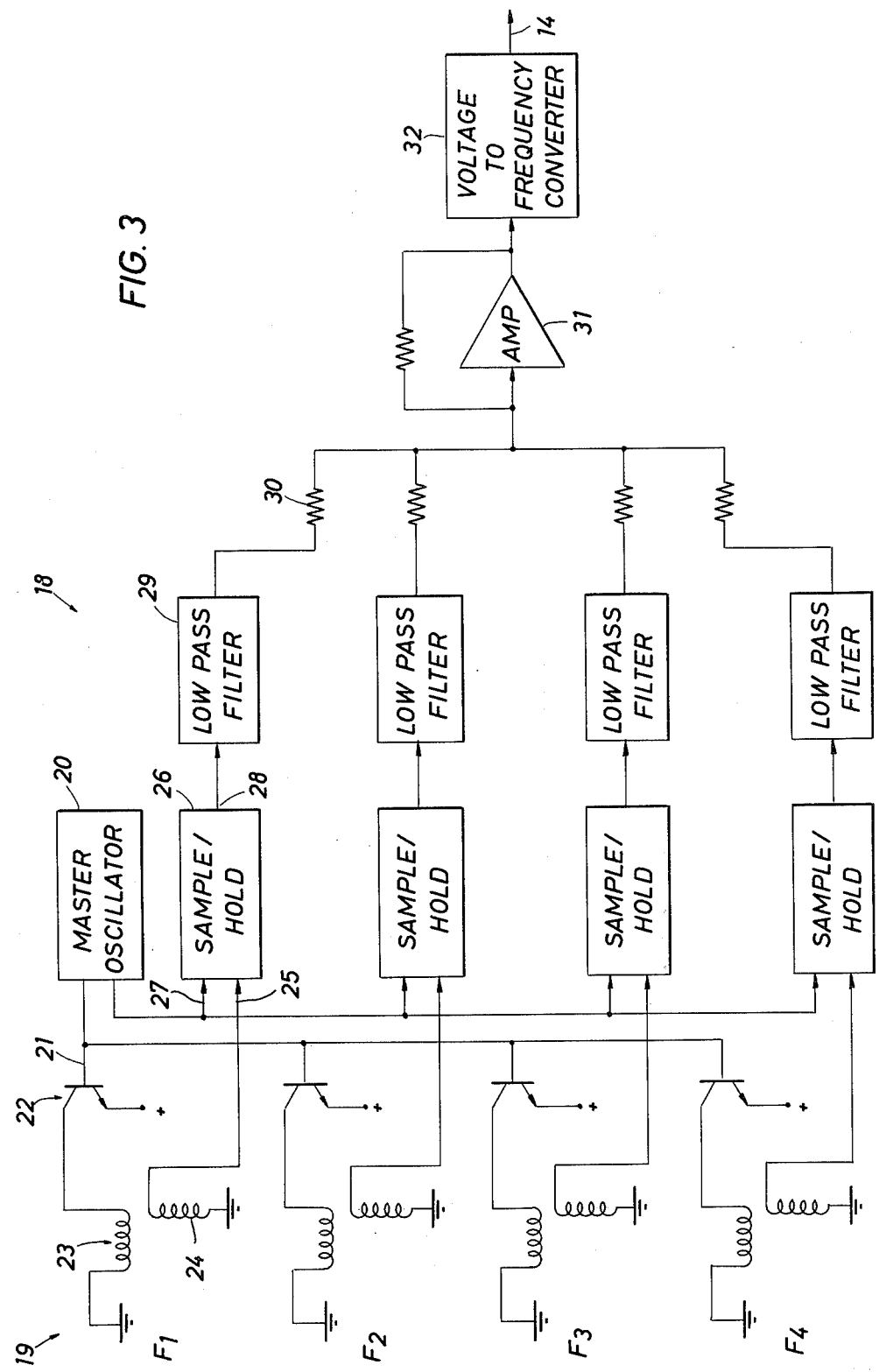
FIG. 3 is a more detailed schematic representation of the flux gate assembly and the subsurface electronics circuitry.

A better understanding of the operation of flux gate assembly 19 of instrument 13 can be had by reference to FIG. 3 which is a schematic illustration of flux gate assembly 19 and subsurface electronics 18. As previously stated, flux gate assembly 19 is comprised of four identical flux gates, $F_1$–$F_4$. Since the associated circuits are identical with respect to each flux gate one such circuit will be described for illustrative purposes. Master oscillator 20 is coupled to base 21 of transistor 22. The output of transistor 22 is connected to one side of drive coil 23 of flux gate $F_1$, the other side of which is connected to ground. Drive coil 23 is wound about a toroidal core and placed within a non-magnetic, metallic housing, as described in my aforementioned copending application. Sense winding 24, of flux gate $F_1$, is connected between ground and the input 25 of sample/hold circuit 26. Sample/hold circuit 26 is further provided with input 27 from master oscillator 20. Output 28 from sample/hold circuit 26 is coupled, to low pass filter 29 the output of which is connected, by way of resistor 30, to the input of amplifier 31. It should be appreciated that the input of amplifier 31 will represent the cumulative flux density measurement as provided by all four flux gates and the associated circuitry. The output of amplifier 31 is coupled to voltage-to-frequency converter 32 the output of which is connected to logging cable 14 for transmittal to the surface.

In the operation of the circuitry of FIG. 3, master oscillator 20 provides a square wave drive input, shown in timing diagram FIG. 4a. Square wave 4a will be coupled to drive coil 23 of flux gate $F_1$, by the switching operation of transistor 22. Drive signal 4a will simultaneously be coupled to the other flux gates in a like manner. The presence of the square wave drive signal at drive coil 23 will result in the core (not shown) of flux gate to be alternately saturated and unsaturated. As is well known in the operation of a flux gate, in the unsaturated state the external flux field impinging the flux gate will enter the core generating an electromotive force proportional to the impinging flux field. The saturating cycle of the square wave operates to prohibit the entry into the core of any external flux field. The sense coil 24, provides the measured flux field input 25 to sample/hold circuit 26. Simultaneous with the measured flux field input, there is provided by input 27 a synchronization pulse, FIG. 4b, from master oscillator 21. Coincidence of synchronization signal 4b and flux gate output 4c results in sample/hold 26 measuring the value of flux gate output 4c for the duration of coincidence with pulse 4b. Sample/hold output 28 is a d.c. level signal functionally related to the flux density as measured by flux gate $F_1$. Output 28 of sample/hold circuit 26 is coupled to low pass filter 29 which is used to remove any small fluctuations in the signal which may be present due to minor irregularities or anomalies in the casing. The filtered output of low pass filter 29 is inputted by way of resistor 30 to summing amplifier 31. The input of amplifier 31 represents constituents of the flux field as provided by all four flux gates, $F_1$–$F_4$, of the flux gate assembly 19. The summed output of amplifier 31 is coupled to voltage-to-frequency converter 32 where it is converted from a d.c. voltage level, functionally related to the measured flux field density within the borehole, to an alternating frequency signal likewise related to the measured flux density. Such conversion is for ease of transmission by way of cable 14 to surface electronics 16. Upon arrival of the signal from subsurface instrument 13 at surface electronics 16, the signal is reconverted to a d.c. level signal functionally related to the measured flux density and is recorded on recorder 17 in relation to the depth at which the measurement occurred.

The overall operation of the system just described can easily be understood by reference to FIG. 5, which is a simplified representation of instrument 13 adjacent a corrosion spot 33 within a section of casing 12. As previously stated, current will flow longitudinally within casing 12. At corrosion spot 33 the current will exit casing 12 flowing into the formation 10. The loss of current from casing 12 results in iron being carried into solution thereby further increasing the corrosion process. The longitudinal current flow within casing 12 causes the establishment of a flux field proportional to and at a right angle from the current flow. Flux gate, F, will detect the flux density within the borehole. As flux gate F comes proximate corrosion spot 33, there will be a measurable decrease in the flux field density due to current loss from casing 12 into formation 10. The decrease in the measured signal will be proportional to the extent of corrosion. By using a plurality of flux gates spaced about the same elevation in the casing there will be a reinforcing action in the measured flux signal.

In an alternate embodiment of instrument 13, as shown in FIG. 6, an orientation section 34 is provided.

Orientation section 34 may be a gyroscope which is oriented at the surface and that maintains, via suitable gimbal mounting rings, its directional orientation throughout the traverse of the logging tool into and out of borehole 11. Or, it may be a suitable compass such as a flux gate compass that is allowed to orient itself with respect to the earth's magnetic field. Both types of direction indicators and their use with down-hole instruments are well known in the art.

As shown in FIG. 6, orientation section 34 is coupled to the signal provided by one of the flux gate circuits. The combination of an orientation signal with one flux gate measurement allows for determination of the orientation or relative direction on the casing at which corrosion occurs. Such information can be used in maximizing the cathodic protection plan to be used on a particular well.

Many modifications and variations besides those specifically mentioned may be made in the techniques and structures described herein and depicted in the accompanying drawings without departing substantially from the concept of the present invention. Accordingly, it should be clearly understood that the forms of the invention described are illustrated herein and exemplary only, and are not intended as limitations on the scope of the present invention.

The embodiments of the invention in which an exclusive property or privilege is claimed are defined as follows:

1. Apparatus for locating corrosion on ferromagnetic casing vertically traversing subsurface earth formations by measuring the magnetic flux density resulting from the longitudinal flow of d.c. galvanic current within said casing; comprising:

an elongated body member adapted to traverse said casing;

a plurality of flux gates positioned within said body member and aligned with the axis of sensitivity of each of said flux gates at a right angle to said longitudinal galvanic current flow for detecting the magnetic flux density resulting from said galvanic current flow, each of said flux gates comprising a drive coil and a sense coil;

a plurality of sample and hold circuits, each of said sample and hold circuits connected to a sense coil for providing a plurality of d.c. signals functionally related to the detected magnetic flux density;

an oscillator circuit switchably connected to said drive coils and connected to said sample and hold circuits for providing a drive signal to said drive coils and a synchronization signal to said sample and hold circuits;

a plurality of filter circuits, each filter circuit connected to a sample and hold circuit; and a summing amplifier connected to said plurality of filter circuits providing an output voltage signal functionally related to the composite of the d.c. signals, said composite voltage signal representing the magnetic flux density resulting from said galvanic current flow; and means for transmitting said composite voltage signal to a surface location.

2. The apparatus of claim 1, further comprising a voltage-to-frequency converter circuit connected to said summing amplifier for converting said composite voltage signal to a frequency based signal.

3. The apparatus of claim 2, further comprising orientation means coupled to one of said plurality of flux gates for providing an indication of the orientation of said corrosion on said casing.

* * * * *